United States Patent [19]

Silverman et al.

[11] Patent Number: 5,082,002
[45] Date of Patent: Jan. 21, 1992

[54] AUTOMATIC OPERANT CONDITIONING SYSTEM ESPECIALLY FOR SCOLIOSIS

[75] Inventors: Gordon Silverman, New York, N.Y.; Barry Dworkin, Hershey, Pa.

[73] Assignee: The Rockefeller University, New York, N.Y.

[21] Appl. No.: 357,463

[22] Filed: May 25, 1989

[51] Int. Cl.$^5$ .................................. A61B 5/103
[52] U.S. Cl. ................... 128/781; 128/78; 128/905; 273/188 R; 340/573; 364/413.02
[58] Field of Search ............. 128/78, 732, 774, 781, 128/905; 273/183 R, 183 B, 187 R, 188 R; 340/573; 364/413.02; 434/247

[56] References Cited

U.S. PATENT DOCUMENTS

| | | | |
|---|---|---|---|
| 4,055,168 | 10/1977 | Miller et al. | 128/905 |
| 4,170,225 | 10/1979 | Criglar et al. | 128/732 |
| 4,337,049 | 6/1982 | Connelly | 273/183 R |
| 4,493,328 | 1/1985 | Saito | 128/905 |
| 4,566,464 | 1/1986 | Piccone et al. | 128/732 |
| 4,683,891 | 8/1987 | Cornellier et al. | 128/905 |
| 4,730,625 | 3/1988 | Fraser et al. | 128/905 |
| 4,846,462 | 7/1989 | Regnier et al. | 340/573 |

OTHER PUBLICATIONS

"μP-Based System Monitors Cable Tension in Spine-Curvature-Victim Treatment", Digital Design, vol. 6, No. 5, May, 1976, pp. 28-32.

Primary Examiner—Lee S. Cohen
Assistant Examiner—K. M. Pfaffle
Attorney, Agent, or Firm—Wyatt, Gerber, Burke and Badie

[57] ABSTRACT

A system and method for the operant conditioning of subjects using biofeedback includes means to measure a variable condition, such as posture, which is controllable by the subject. The apparatus sets criteria which, if not met, may result in a negative reinforcement, such as unpleasant audio tone or, if the criteria is met, will reward the subject. The criteria is automatically adjusted, upwards or downwards, in accordance with the subject's history of reaching, or not reaching, the criteria.

One embodiment is a device for the training of patients with idiopathic scoliosis (curvature of the spine), as a replacement for a brace. The device includes two cables, one about the chest to measure breathing and the other longitudinally about the trunk to measure spine length. The variable lengths of the cables are converted to digital signals by rotary-to-digital converters. The device includes a programmed microcomputer whose inputs are the digital converters which automatically adjusts the criteria and which controls a tone generator and its speaker to provide an audio feedback of out-of-criteria postures.

12 Claims, 6 Drawing Sheets $Rh \equiv Rhigh$
$Rl \equiv Rlow$

AUTOMATIC OPERANT CONDITIONING SYSTEM ESPECIALLY FOR SCOLIOSIS

BACKGROUND OF THE INVENTION

1. Field of the Invention

The present invention relates generally to the biofeedback training using an automatic system for operant conditioning, and more particularly to a medical instrument to be worn by patients with scoliosis (curvature of the spine).

2. Description of the Related Art

The present invention relates, in its broad aspects, to the field in experimental psychology known as operant conditioning. An article in this field is "Shaping By Automated Tracking Of An Arbitrary Operant Response", by Pear and Legris, *Journ. Experimental Analysis of Behavior*, No. 2, March 1987, pgs. 241-247, which describes the training of pigeons to peck at a target by rewarding the pigeons with food when they pecked at the target. The process is called "shaping" of "operant responses" because closer approximations to the target are rewarded ("reinforced"). The subject must continually improve in order to gain the reward. In the Pear-Legris article the size of the target was made smaller, which made the pigeons improve in finding the target and the birds' movements were recorded using two TV-cameras connected to a microcomputer. The article concludes that "current knowledge of what happens during shaping is primarily qualitative and not easily communicated . . ."

An improved and microcomputer controlled automatic operant shaping process and system is envisioned to be applicable to various fields. For example, in the field of human physical rehabilitation training involving the skeleton-muscle system, it may be used to correct the walking gait of stroke patients. Another use may be as a respiration trainer for post-surgical patients who fail to breathe deeply enough following their operation. Other examples include its employment as a type of biological feedback to modify visceral functions, such as blood pressure and sensory motor rhythms. Outside of the field of medicine, operant response conditioning may be employed to improve sports performance and "small motor" tasks, i.e., hand tasks, such as keyboard entry learning.

The particular application of the present invention, discussed as an embodiment, is the treatment of idiopathic scoliosis, which is the pathologic lateral curvature of the spine. Idiopathic scoliosis, it is reported, affects 2-4% of adolescents, 80% of whom are female, and at least 6% of those affected have a truncal deformity which grows worse throughout adolescence. The usual treatment is for the patient to wear a brace, such as the Milwaukee brace, which fits around the chest and neck. The brace should be worn 23 hours a day, 7 days a week, from 2-4 years. Young girls hate wearing such braces, and often refuse or neglect to do so. Even those who manage to wear braces suffer. Sometimes the brace, in restricting truncal motion, may cause the trunk muscles to weaken or atrophy. The brace's constant pressure causes deformation of the rib cage or soft tissue on which the brace rests.

U.S. Pat. No. 4,055,168 to Neal Miller and Barry Dworkin, assigned to Rockefeller University, and the article "Behavioral Method For the Treatment of Idiopathic Scoliosis", by Dworkin, Miller et al, *Proc. Natl. Acad. Sci.*, Vol. 82, pgs. 2493-2497, April 1985, both incorporated by reference, describe a posture training device for the treatment of idiopathic scoliosis. In that device one cable (body harness cord) extends around the chest of the patient to monitor respiration and a second cable extends around the longitudinal axis of the body from the pubis to the scalpula. Both cables are connected at their ends, in one embodiment, to slidable plates and in another embodiment to rotary potentiometers.

Although that posture training device was relatively successful on groups of test patients, compared to the treatment using braces, the device has not been commercially produced.

OBJECTIVES AND FEATURES OF THE INVENTION

It is an objective of the present invention to provide a method and system for use in biofeedback operant conditioning in which the subject's responses will be automatically obtained and the target conditions will be automatically and appropriately adjusted.

It is a further objective of the present invention to provide such a method and system in which the biofeedback is subject to program control which controls the density of the reinforcement feedback and, if the reinforcement is negative, adjusts it to within the tolerance of the subject, within upper and lower limits.

It is a still further objective of the present invention to adjust the feedback according to criteria, which is adjustable, so that the adjustments in the criteria track the subject responses, the closeness of such tracking also being selectable.

It is a further objective of the present invention, in the embodiment of a posture training device for the treatment of idiopathic scoliosis, to provide a device which permits the patient to move normally and without the confinement or embarrassment of a brace, whose warning signal of poor posture is not an embarrassment to the patient, and which provides a carefully programmed series of positive reinforcement rewards and negative reinforcement in a programmed series of changes in the criteria of acceptable posture, responsive to improvements and non-improvements, to enable the patient to attain an increasingly improved posture.

It is a feature of the present invention to provide a method and system for the training of subjects by biofeedback operant conditioning using a device worn by the subject. The method includes the steps of measuring for each time interval a body function variable R which changes and which the subject may control through effort. For example, the time intervals are sample periods of one second. The measurement is converted into digital data and communicated to a microcomputer within the device. The microcomputer automatically calculates an adjustable criteria C for the body function.

The microcomputer controls a feedback stimulus to the subjects, such as an audio tone, if the body function R does not meet the adjustable criteria C. The criteria C are automatically adjusted by the device to higher values when R exceeds C and to lower values when R is less than C, within upper and lower bounds for C. The variable R may be a calculated composite of two variable body functions, namely, automatic body function, such as breathing, and a conscious controllable body function, such as posture (spinal length).

It is a further feature of the present invention to provide a portable device for the treatment of patients having idiopathic scoliosis. The device is worn by the patient and uses biofeedback to improve the posture of the patient. The device includes one cable removably positioned around the chest of the patient to measure respiration (RES) and another cable longitudinally around the trunk of the patient to measure the length of the spine. The device has two transducer means connected to the cables to convert the expansion and contraction lengths of the cables and convert those changes in length into digital electrical signals. A digital microcomputer is connected to the transducers and has digital programmed memory and additional digital memory. The device has a feedback stimulus means, such as an audio tone, controlled by the microcomputer to stimulate the patient for training reinforcement. The microcomputer has computation means to compute an actual effective spine length R during sample periods where $R = T - K \cdot RES$, T being the original in-posture spine length and K being the coefficient of coupling between T and RES; and control means to control the stimulus means so that the stimulus is applied only if $R < C$ where C is an adjustable criterion. The microcomputer also had adjustment means to automatically adjust C based upon prior R and C relationship.

SUMMARY OF THE INVENTION

In accordance with the present invention, there is provided a method and system to obtain improved training using biofeedback operant conditions, in which a microcomputer controlled device automatically responds to changes by a subject. The device is an automatic training or teaching instrument which shapes the subject's behavior. One embodiment is a patient-worn device for posture training in the treatment of idiopathic scoliosis. The device is battery operated and has two cables, one around the chest to monitor respiration and the other longitudinally about the trunk to monitor spinal length. Each cable has an end fixed at the device and a pullable end connected to a springloaded distance transducer. The transducers are preferably shaft encoders which are rotary motion to digital signal converters.

The device measures the posture of the subject, as monitored by the longitudinal trunk cable, taking account of respiration, as monitored by the chest cable. When the patient's posture is poor, a warning may be given, subject to the amount of the patient's prior poor performance, so that continued bad posture will provoke a warning signal, preferably an annoying tone sound audible to the patient.

The device is programmed, in accordance with the present invention, to provide what appears to the subject to be a random time period between the onset of bad posture and the start of the warning signal. That time period will vary depending on the amount of "credit" for good posture (within-criteria time) that has been accumulated by the subject in the reward timer. The device does not provide an immediate warning signal on the onset of bad posture, except if the subject has no "credit" in the reward timer, because such an immediate signal (tightly coupled time frame) would stress and irritate the subject. For good posture, the device is programmed to provide an instantaneous feedback, i.e., a tight coupled time frame of less than 1 second, so that good posture will immediately turn off the warning signal (negative reinforcer). The device automatically monitors and registers, in its memory, the amount of time the patient is out of correct posture and the amount of the time the warning is on. If the warning time is too long, for example, over 10% in any hour (over 6 minutes) the criteria of what constitutes poor posture is lowered until a lower limit (lower criteria Lc). Conversely, if the patient does well for a time period, for example, one hour, the posture criteria is raised to an upper limit (upper criteria Uc). The upper criteria (Uc) and lower criteria (Lc) are not fixed, but rather are a band which is automatically changed, for example, daily, depending on the patient's progress. The audio tone, which is the negative reinforcement, is on various tone levels, and the level rises should the patient persist in remaining out of proper posture. However, if the patient maintains good posture, he will build-up "credits", i.e., an accumulation of good posture time, which permits some time period of slouching, i.e., semi-poor posture. The device provides a constantly moving target which is immediately responsive to the subject. For example, if the subject is tired for a period (time epic), for example, one hour, the criterion is lowered.

BRIEF DESCRIPTION OF THE DRAWINGS

Other objectives and features of the present invention will be apparent from the following detailed description, taken in conjunction with the accompanying drawings. In the drawings.

DETAILED DESCRIPTION

System Description

Figure 1:
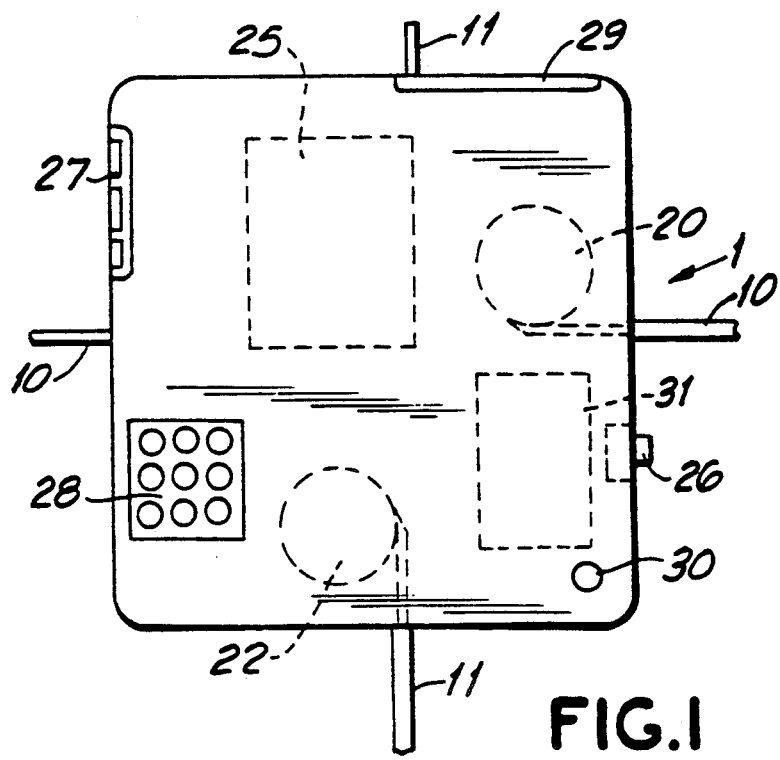
FIG. 1 is a top plan view of the device of an embodiment of the present invention.
Figure 2:
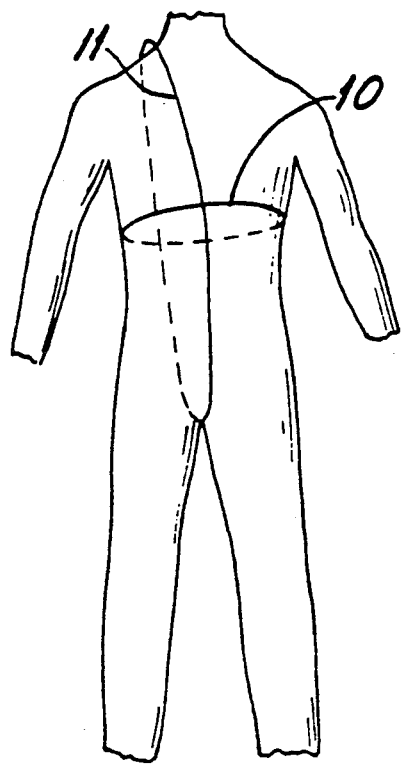
FIG. 2 is a front view of a patient wearing the device of FIG. 1.
Figure 3:
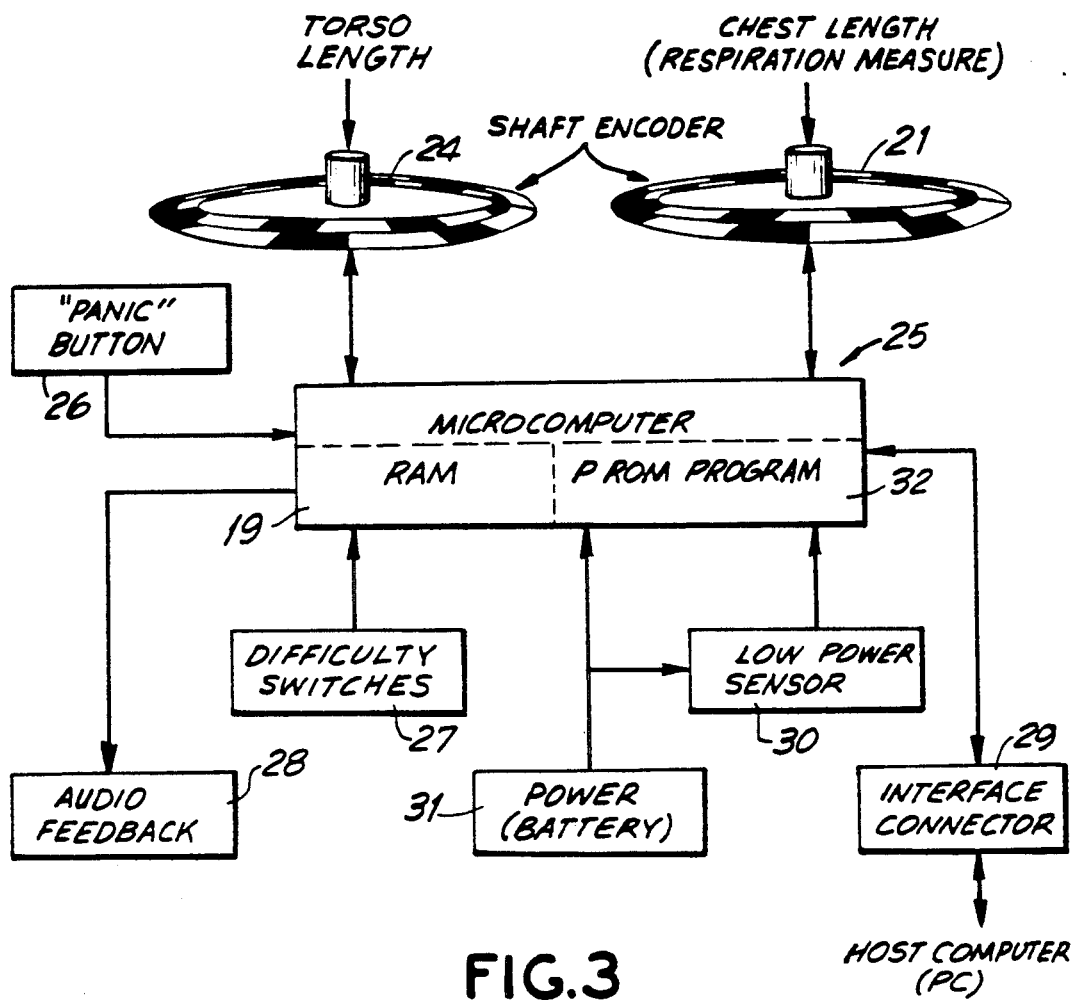
FIG. 3 is a block diagram and partly in perspective of an embodiment of the device of the present invention as shown in FIG. 1.

As shown in FIGS. 1-3, the mechanical construction of the posture training device 1 is similar to the device of U.S. Pat. No. 4,055,168 in having two cables 10 and 11 connected at one of their respective ends to a case 1. The cable 10 extends around the chest and monitors respiration and the cable 11 extends longitudinally about the trunk to measure the spinal length, see FIG. 2.

The cables 10 and 11 each have intermediate buckles (not shown) to permit their fastening and unfastening.

The chest cable 10, which measures the length of the chest, as a respiration measure, at its end, is wound about a spring-loaded bobbin 20 connected to a shaft encoder 21. Similarly the trunk cable, which measures torso length, is wound on spring-loaded bobbin 22 which is connected to a shaft encoder 24. The encoders 21 and 24 are preferably rotary shaft encoders whose absolute (not relative) rotational position is converted by a Gray code by brushes which read conducting and non-conducting regions on the surface of the disks. Alternatively, other types of length to digital data transducers may be used. The digital Gray code electrical signal outputs of the shaft encoders 21 and 24 are converted into conventional binary code by the microcomputer 25. The microcomputer is preferably a NEC7500 which is a large-scale solid-state integrated circuit having an internal PROM program (Programmable Read Only Memory) 32. The various switches, controls and outputs of the device 1 are electrically connected to its internal microcomputer 25.

The signal inputs to the microcomputer 25 include the shaft encoders 21 and 24, the panic button 26 and the difficulty switches 27.

The signal outputs of microcomputer 25 are to the audio feedback 28, which is a piezoelectric tone generator and speaker, and the inteface connector 29 which permits data loading and unloading from a host computer, for example, a personal computer (PC) such as the IBM-AT. A low power sensor 30 indicates when the battery power 31 is low.

The panic button 26 is a button on the device which may be operated by the user. The button 26, when depressed, stops the warning tone. The number of times that the button is depressed for a period, for example, one week, is recorded in the RAM memory 19. After the panic button 26 is pushed, the microcomputer 25 imposes a random delay, preferably between 1–5 seconds, before turning off the audio warning. The purpose of this delay, a loose time relationship between button actuation and deactivation of the audio tone, is to teach the user that it is better to improve his posture, thereby turning off the tone, than to push the panic button.

The warning audio tone is turned off immediately by the microcomputer when the spinal length is within the criteria, as explained below. For example, if the patient corrects his posture, the tone is immediately turned off, within 200 milliseconds and, in any event, less than 1 second.

Operant Response Method

The method is described below, in detail, in connection with the scoliosis device. However, its principles are applicable to other operant response systems and more than two encoders may be similarly combined.

The device obtains samples of the two parameters measured by the encoders. These parameters are "RES", respiration and "T", measured spine length. The samples are taken preferably at least once each second the device is worn by the patient.

The basic equation computed in the device is:

$$R = T - K \cdot RES \qquad \text{Eq. 1}$$

In this equation "R" is the "calculated spine length", i.e., the spine length which is a measure of the spine length, moment-by-moment, taking account of respiration and other factors. "T" is the uncompensated torso length. "RES" is the respiration of the patient, i.e., the patient's chest expansion with each breath. "k" is the coefficient of coupling between T and RES and is a measure of the contamination which is automatically adjusted, as explained below.

The adjustment of k may reduce k to medium levels, for example, between 0.55 and 0.65 where T and RES are on arbitrary scales of 0 to 100.

As an example, without subtraction of the contaminating influence of respiration on spine length, variations in RES from a value of 30 (inspiration or breath in) to a value of 20 (expiration or breath out), might produce variations in T (and hence R) from 68 to 62 when its true length is 50. However, when k is set to 0.6, the calculated value of T will remain 50 (its true value) during both inspiration and expiration.

The microcomputer is programmed to adjust the value of k, shown by the software routine of FIG. 5 as follows. An adjustment "minor epochs" is set by the program, for example, 10 minutes. The processor (microcomputer and its inputs) measures R and stores, in its memory, the values of R. The values of the highest (R high) and lowest (R low) are retained in memory. After the series of minor epochs, for example, each hour, the adjustment is calculated by the formulas Eq. 2 and 3 below:

$$\frac{\text{Sum }(R \text{ high})}{\text{Sum }(R \text{ low})} = S_D \qquad \text{Eq. 2}$$

The sums are over the series of minor epochs.

$$\text{If } S_D > 1.0 \text{ increase k. If } S_D < 1.0 \text{ decrese k} \qquad \text{Eq. 3}$$

The increase or decrease is predetermined and is preferably about 0.01. The limits of k are set at between 0.5 and 0.85.

Figure 5:
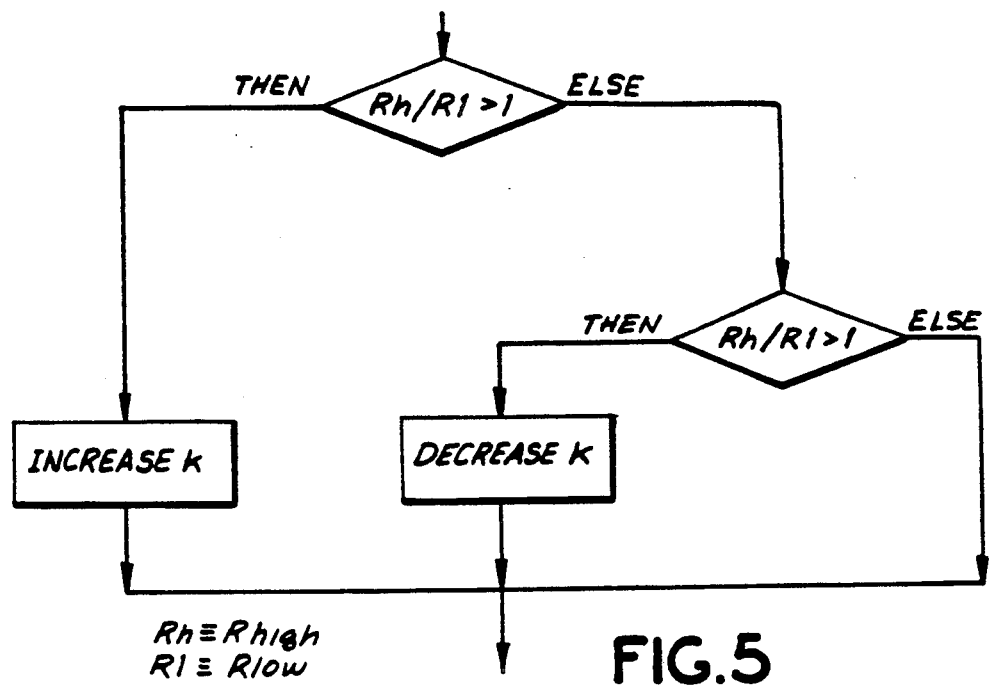
FIG. 5 is a software routine block diagram of the adjustment of k (coupling coefficient)

The above-described procedure for the adjustment of k is illustrated in FIG. 5.

Figure 6:
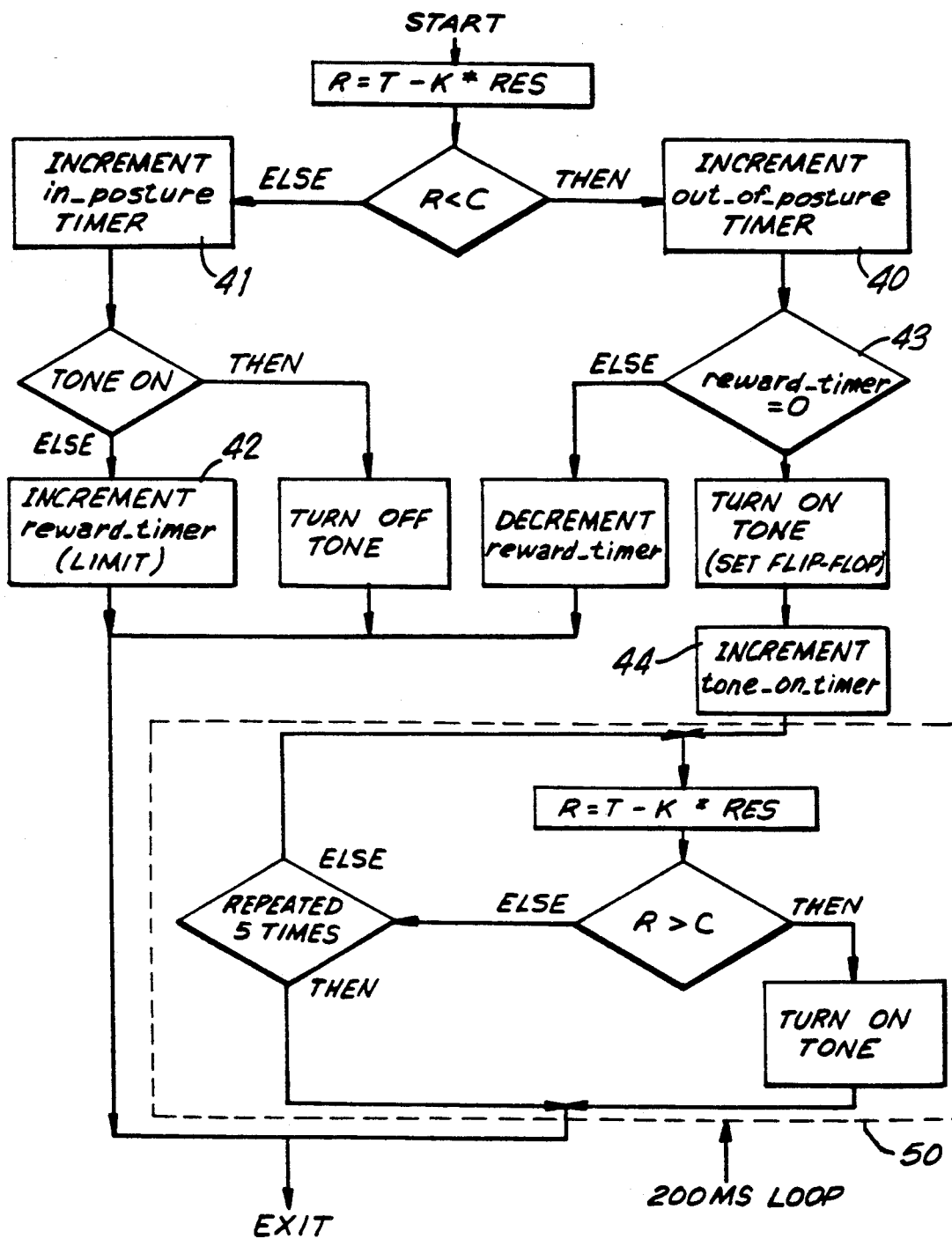
FIG. 6 is a software routine block diagram of the calculation of C (criterion) and tone management.
Figure 7:
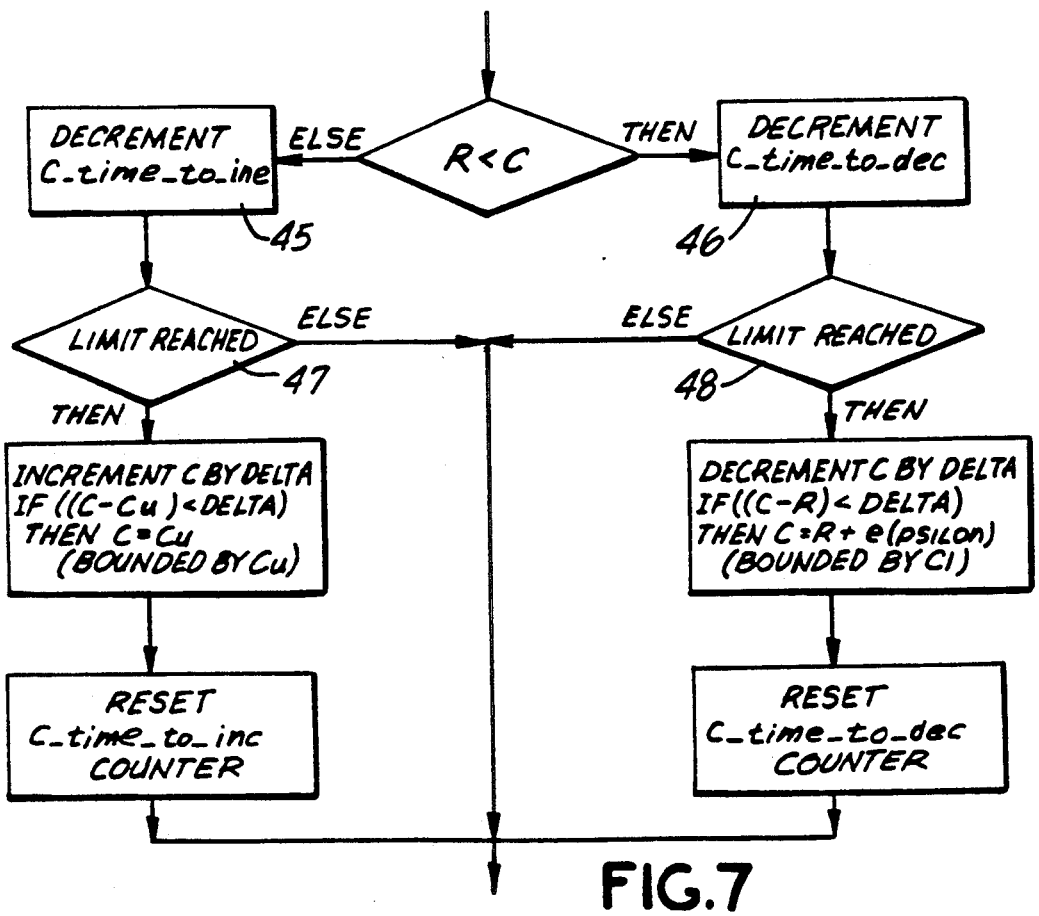
FIG. 7 is a software routine block diagram of the adjustment of C (criteria)

The microcomputer calculates R (effective length) for each sample. A sample duration, for example, is one second. As shown in FIG. 6, the calculation of R controls the tone, i.e., audio tone signal which is produced by the speaker within the device 1. R, for each sample, is compared to "C", which is a calculated number defining an acceptable posture, i.e., C is a standard defining an out-of-posture value. C is not constant, but is adjusted automatically by the microcomputer, as explained below. If R is less than C for a sample, i.e., the posture is below the accepted limit of C, the out-of-posture timer 40 is actuated. If R is greater than C, i.e., the posture is acceptable during the sample period, the in-posture timer 41 is actuated. If the tone is already on, the acceptable posture (R>C) turns it off. If the tone is off, then the acceptable posture (R>C) is timed and accumulated by the reward timer 42, which has a preset maximum, for example, 20 seconds. The various timers (counters) 40, 41 and 45, 46, see FIG. 7, are programmed counter functions of the microcomputer, as are the other timers (counters).

On the other hand, if R<C, and the reward timer 42 has accumulated 0 time rewards, then the tone is turned on, i.e., the tone control flip-flop is set, which increments the tone-on-timer 44. In addition, an inner loop 50, 200 MS in duration, is actuated (shown by dot-dot line in FIG. 6). R is recalculated with the inner loop 50. If R>C (posture acceptable) the tone is turned off. If the posture stays unacceptable (R<C), the loop is repeated 5 times (1 second) before resuming the program.

Generally, the subject is simply told that his actions are, or are not, obtaining the desired target goal. For example, the patient is informed if his blood pressure is falling or rising.

An important element of the present invention is the automatic adjustment of C, the standard for an acceptable posture. The active control and management of C (acceptable posture) is central to the shaping of behavior. If C were to be static, as is often the case in biofeedback systems, the most efficient shaping of behavior would not occur. The programmed microcomputer presents a moving target, i.e., an ever-changing C. The definition of what constitutes an acceptable posture, so as to not turn on the tone, is automatically changed (adjusted).

As shown in FIG. 7, the changes in C are in response to the patient's maintaining acceptable posture, or failing to maintain acceptable posture. R may be less than C, i.e., R<C (measured posture R worse than adjustable criteria C for a sample period, for example, 1 second). The times R<C and R>C are recorded in counters 45, 46. If either times (below or above C) exceeds a pre-set time limit, C is adjusted. The amount of time set by the limits of counters 45, 46 (47, 48) determine how often C is changed, i.e., the fineness of the gradations in C. Preferably the limits of limit counters 45, 46 are in the range of 10–30 minutes, preferably 20 minutes.

When the time limits in counters 45, 46 are reached, C is changed by "Delta", which is a predetermined amount. For example, where C is on a scale of 0 to 100, then Delta is in the range of 1–5, and is preferably 1. However, there is no change to C if its predetermined upper limit Cu (upper bound of C) or lower limit ($C_L$ lower bound of C) would be reached. For example, if the limit 47 is exceeded because posture has been good for over 10 minutes, then C is adjusted upwardly (increment) by one unit, unless C is already equal to Cu (upper bound). Conversely, if limit 48 is reached C may be decremented, as explained below, unless $C_L$ (lower bound) has been reached. After C is adjusted the limit counters 45, 46 are reset to their original limits, i.e., 20 minutes.

The predetermined adjustment amount Delta, for example, 1 unit, is satisfactory for periods of acceptable posture. Adjustments of C using a fixed Delta provides a constantly higher definition of C (acceptable posture). For example, if C starts at 70 and the patient has 20 consistent periods of acceptable posture (R>C) then C is adjusted to 90. The adjustment upwards of C stops at its upper limit (Cu), for example, at 90.

However, a fixed adjustment amount is unsatisfactory for the decrement adjustments. A fixed decrement amount would reward bad posture. Instead, until the lower bound ($C_L$) is reached, C is adjusted downwardly (decrement) by the formula:

Decrement by Delta if C−R>Delta    Eq. 4

If C−R<Delta then calculate C as C=R+e(psilon)    Eq. 5

As an example of Eq. 4, if C starts at 70 and R is measured at 65, and Delta is 1, then C−R (5)>Delta (1) so the decrement adjustment to C is 1, C becomes 64. As an example of Eq. 5, if C starts at 70 and R is measured at 69, then C−R (1)=Delta (1) so that the decrement is not Delta but e(psilon), which is fixed but is less than Delta, for example ½. C is adjusted to 69.5 and continuing bad posture has not been rewarded as R remains below C, so that the tone may remain on. No criterion adjustment decrement C is made such that C is less than or equal to R. Thus, the adjustment does not act as a reinforcer to the bad posture behavior.

Figure 8:
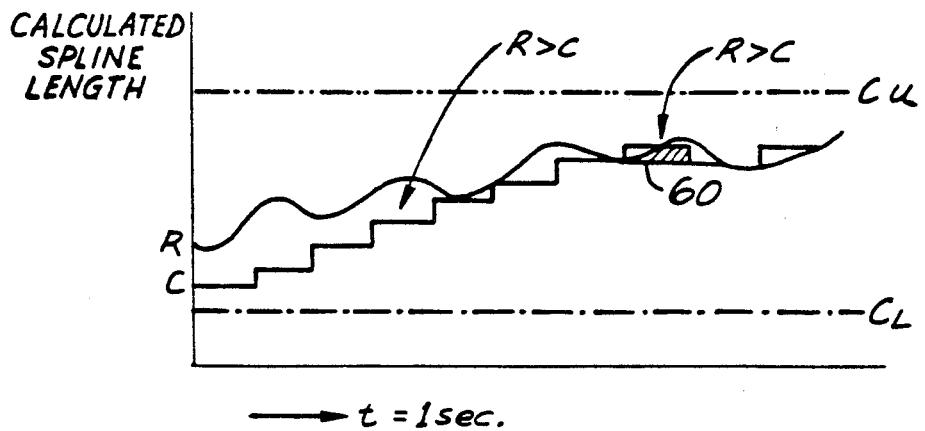
FIG. 8 is a chart plotting arbitrary scale units against time.
Figure 4:
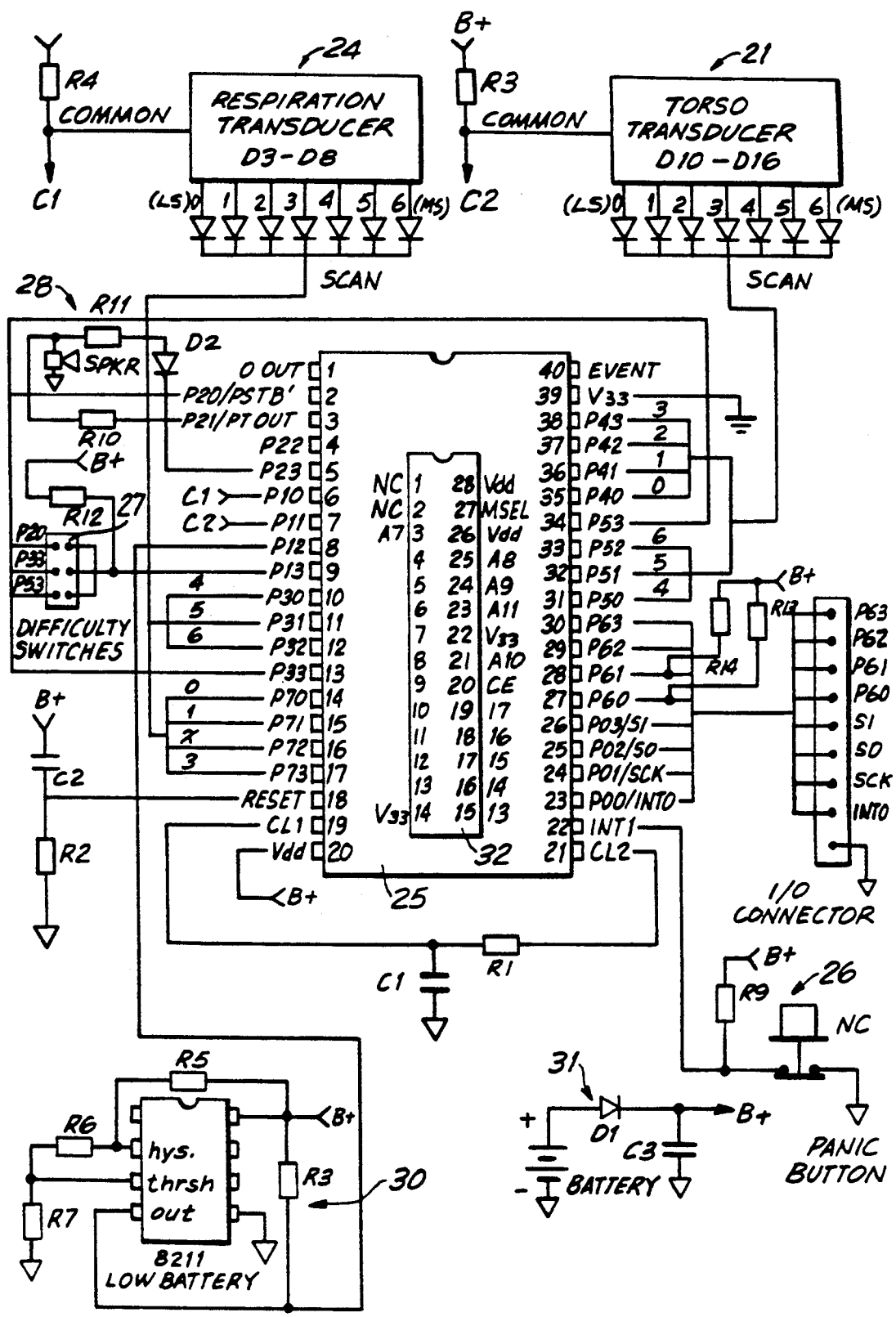
FIG. 4 is a circuit diagram of circuitry of FIG. 3.

In FIG. 8, the curve of R, as measured over time t of 1-second samples, is shown as gradually increasing in a non-linear manner. C (criterion) is progressively increased in 1 unit steps between Cu (upper limit) and $C_L$ (lower limit). At position 60, R has dropped below C (cross-hatched lines) and consequently C is decremental.

Figure 9:
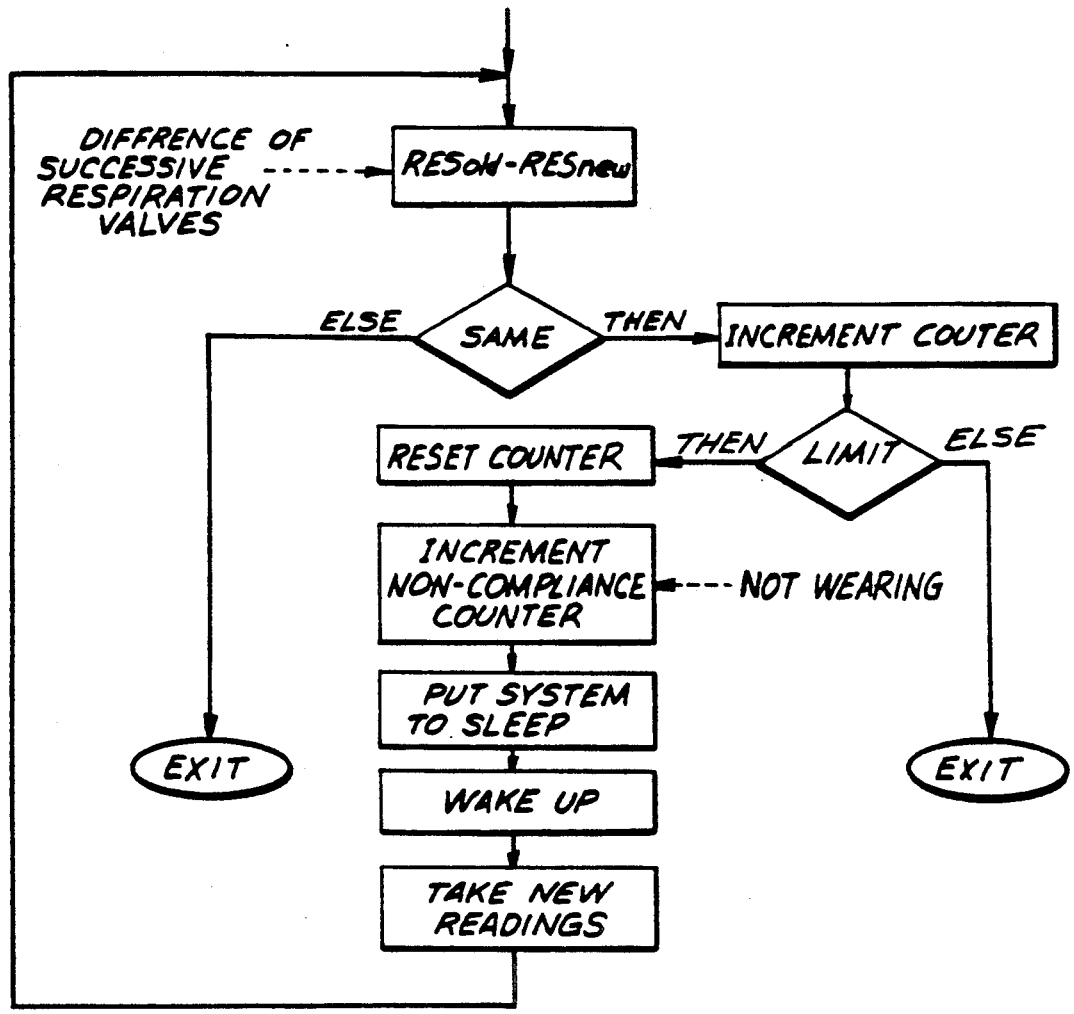
FIG. 9 is a software routine block diagram of the compliance (use of the device)

FIG. 9 illustrates a suitable software routine to measure compliance. In the context of the posture training device, compliance is the amount of time that the subject wears the device, regardless of the subject's posture, and non-compliance is the amount of time the subject does not wear the device. For example, if a subject is supposed to wear the device almost all the time, even while sleeping, and the non-compliance time amount is over 20 hours a week, it indicates that the subject has not followed instructions in wearing the device. The device, in effect, looks at the cable around the chest and sees if it moves as it would during normal breathing (respiration RES). If the measured times between chest cable movements, which is RES old-RES new, is more than one minute, then the cable length is not being changed and the device is not being worn.

As shown in FIG. 9, the difference of successive respiration values increments an increment counter. If the limit is exceeded, the counter is reset and the non-compliance counter is started. This indicates that the device is not being worn. In addition, in order to save battery energy, part of the system is, in effect, put "to sleep" in that, as a result of the software routine shown in FIG. 9, the multiplexer samples input data only once a minute instead of at its ordinary (non-sleep) input data sampling rate of once per second. The system will, under clock control, after a pre-set period, for example, one minute, automatically "wake-up", i.e., go to its regular data sampling rate to take new readings. If the new readings still show that the device is not being worn, part of the system will again be put "to sleep". The repeated putting to sleep of part of the system saves battery energy.

Figure 10:
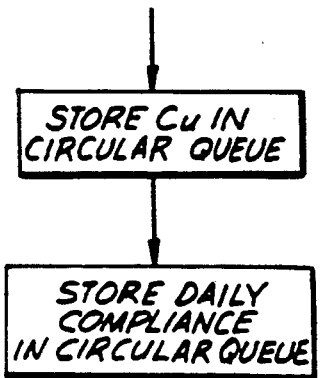
FIG. 10 is a software routine block diagram of record keeping (storage of performance and compliance times).

FIG. 10 illustrates the software routine for record keeping. Counters in the device accumulate the subject's level of performance and time of compliance. The subject's performance is measured by the value of Cu attained each day. This is a stable and convenient measure of performance. The subject's compliance time, i.e., the time the device is worn, is measured by the non-compliance counter. Preferably, the performance measure (Cu) and compliance times are accumulated each day. The device uses 16 counters which are able to accumulate the most recent 16 days of data. This is the "circular queue" of FIG. 10 in which the counters form a circular buffer. The counters should be accessed and the data transferred to the host computer, i.e., downloaded, before the 16 days expire, through the interface 29 of the device.

In addition, another counter is used as a yearly cumulative counter. This counter will record the overall times the subject has been in compliance.

We claim:

1. A portable apparatus for the treatment of a patient having a posture characterized by idiopathic scoliosis, said apparatus to be worn by the patient and utilizing biofeedback to improve the posture of the patient, the apparatus comprising:
(a) a first cable which is expandable and contractable and is adapted to be removably positioned around the chest of the patient to measure respiration (RES);
(b) a second cable which is expandable and contractable and is adapted to be removably positioned longitudinally around the trunk of the patient to measure the greater circumference of the trunk;

(c) first and second transducer means connected to said first and second cables respectively to measure changes in the expansion and contraction of the respective cables and convert said chances into digital electrical signals;

(d) a digital microcomputer connected to said transducer means to receive said digital signals and having digital programmed memory and additional digital memory;

(e) a feedback stimulus means controlled by the microcomputer to stimulate the patient for reinforcement by applying a stimulus to the patient;

(f) computation means to compute an actual effective spine length R during sample periods where $R = T - K \cdot RES$, T being a spine length during proper posture of the patient and K being a coefficient of coupling between T and RES; and (g) control means to control said feedback stimulus means so that the stimulus is applied only if $R < C$ where C is an adjustable criteria;

(h) adjustment means to automatically adjust C based upon the prior history of R and C of the patient;

(i) compliance means to determine if the apparatus is being worn by the patient; and (j) multiplexing means to sample data from said first and second transducer means and power saving means to control said multiplexing means so the multiplexing means samples data at a slower rate if the compliance means has determined that the apparatus is not being worn.

2. Apparatus as in claim 1 wherein said multiplexing means samples data at 10-200 times per minute.

3. A portable apparatus for the treatment of a patient having a posture characterized by idiopathic scoliosis, said apparatus to be worn by the patient and utilizing biofeedback to improve the posture of the patient, the apparatus comprising:

(a) a first cable which is expandable and contractable and is adapted to be removably positioned around the chest of the patient to measure respiration (RES);

(b) a second cable which is expandable and contaractable and is adapted to be removably positioned longitudinally around the trunk of the patient to measure the greater circumference of the trunk;

(c) first and second transducer means connected to said first and second cables respectively to measure changes in the expansion and contraction of the respective cables and convert said changes into digital electrical signals;

(d) a digital microcomputer connected to said transducer means to receive said digital signals and having digital programmed memory and additional digital memory;

(e) a feedback stimulus means controlled by the microcomputer to stimulate the patient for reinforcement by applying a stimulus to the patient;

(f) computation means to compute an actual effective spine length R during sample periods where $R = T - K \cdot RES$, T being a spine length during proper posture of the patient and K being a coefficient of coupling between T and RES;

(g) control means to control said feedback stimulus means so that the stimulus is applied only if $R < C$ where C is an adjustable criteria;

(h) adjustment means to automatically adjust C based upon the prior history of R and C of the patient;

(i) compliance means to determine if the apparatus is being worn by the patient; and (j) counter means connected to said compliance means to accumulate data representing time periods when the patient wears the apparatus.

4. Apparatus as in claim 3 wherein said first and second transducer means the rotary-to-digital converters.

5. Apparatus as in claim 3 wherein said microcomputer includes internal Programmable Read Only Memory containing the instructions of the computation means and adjustment means.

6. Apparatus as in claim 3 wherein said stimulus means includes a tone generator and an audio speaker connected to said tone generator.

7. Apparatus as in claim 3 wherein said tone generator produces a plurality of tones.

8. Apparatus as in claim 3 wherein K is adjustable and the apparatus further includes a second adjustment means to adjust K.

9. Apparatus as in claim 3 and further including a reward counter means to accumulate the time the patient has maintained correct posture and to decrement the time the patient has not maintained correct posture, and wherein said stimulus is acativated only if the reward counter means has an insufficient accumulation of time that the patient has maintained correct posture.

10. Apparatus as in claim 3 and further including band setting means to set upper and lower limits on C.

11. Apparatus as in claim 3 and further including a second counter means to accumulate data representing the performance of the patient which is the maximum daily performance.

12. Apparatus as in claim 3 wherein said compliance means comprises measurement means connected to said first transducer means to measure the number of respirations of the patient within a predetermined time period.

* * * * *